(12) United States Patent
Opsal et al.

(10) Patent No.: US 6,465,265 B2
(45) Date of Patent: Oct. 15, 2002

(54) ANALYSIS OF INTERFACE LAYER CHARACTERISTICS

(75) Inventors: Jon Opsal, Livermore; Jingmin Leng, Fremont, both of CA (US)

(73) Assignee: Therma-Wave, Inc., Fremont, CA (US)

( * ) Notice: Subject to any disclaimer, the term of this patent is extended or adjusted under 35 U.S.C. 154(b) by 7 days.

(21) Appl. No.: 09/804,765

(22) Filed: Mar. 13, 2001

(65) Prior Publication Data

US 2002/0045282 A1 Apr. 18, 2002

Related U.S. Application Data

(60) Provisional application No. 60/266,912, filed on Feb. 7, 2001, and provisional application No. 60/189,744, filed on Mar. 16, 2000.

(51) Int. Cl.$^7$ .......................... H01L 21/66; G01B 11/06
(52) U.S. Cl. .......................................... 438/16; 356/632
(58) Field of Search ..................... 438/14, 16; 356/625, 356/630, 632

(56) References Cited

PUBLICATIONS

D.E. Aspnes et al., "Optical Properties of the Interface between Si and Its Thermally Grown Oxide," *Physical Review Letters*, vol. 43, No. 14, Oct. 1, 1979, pp. 1046–1050.

G.A. Candela et al., "Preparation and Certification of SRM–2530, Ellipsometric Parameters Δ and ψ and Derived Thickness and Refractive Index of a Silicon Dioxide Layer on Silicon," *U.S. Department of Commerce/National Institute of Standards and Technology*, NIST Special Publication 260–109, Issued Oct. 1988, pp. coverpage, I,. & 1–37.

G.E. Jellison, Jr., "Examination of thin $SiO_2$ films on SI using spectroscopic polarization modulation ellipsometry," *J. Appl. Phys.*, vol. 69, No. 11, Jun. 1, 1991, pp. 7627–7634.

B.J. Mrstik et al., "Measurement of the Thickness and Optical Properties of Thermal Oxides of Si Using Spectroscopic Elliposmetry and Stylus Profilometry," *J. Electrochem. Soc.*, vol. 138, No. 6, Jun. 1991, pp. 1770–1778.

S.J. Fang et al., "Comparison of Si surface roughness measured by atomic force microscopy and ellipsometry," *Appl Phys. Lett.*, vol. 68, No. 20, May 13, 1996, pp. 2837–2839.

C.M. Herzinger et al., "Ellipsometric determination of optical constants for silicon and thermally grown silicon dioxide via a multi–sample, multi–wavelength, multi–angle investigation," *Journal of Applied Physics*, vol. 83, No. 6, Mar. 15, 1998, pp. 3323–3336.

T. Easwarakhanthan et al., "Measurement of the Interface Layer Thickness in $SiO_2$/Si Structures by Single–wavelength Null Ellipsometry," *Surface and Interface Analysis*, vol. 26, No. 13, Dec. 1998, Dec. 1998, pp. 1008–1015.

J. Opsal et al., "Broadband spectral operation of a rotating––compensator ellipsometer," *Thin Solid Films*, vol. 313–314, Nos. 1–2, Feb. 1998, pp. 58–61.

I.H. Malitson, "Interspecimen Comparison of the Refractive Index and Fused Silica," *Journal of the Optical Society of America*, vol. 55, No. 10, Oct. 1965, pp. 1205–1209.

T. Yasuda et al., "Optical–standard surface of single–crystal silicon for calibrating ellipsometers and reflectometers," *Applied Optics*, vol. 33, No. 31, Nov. 1, 1994, pp. 7435–7438.

William H. Press et al., "Numerical Recipes," *Cambridge University Press New York*, 1986, pp. coverage, i, & 523–528.

P.G. Snyder et al., "Modeling $Al_xGa_{1-x}As$ optical constants as functions of composition," *J. Appl. Phys.*, vol. 68, No. 11, Dec. 1, 1990, pp. 5925–5926.

*Primary Examiner*—Michael Sherry
*Assistant Examiner*—Evan Pert
(74) *Attorney, Agent, or Firm*—Stallman & Pollock LLP

(57) ABSTRACT

A method is described for analyzing and characterizing parameters of a semiconductor wafer. In particular, an approach is described for characterizing the interface layer between a thin oxide film and a silicon substrate in order to more accurately determine the characteristics of the sample. The wafer is inspected and a set of measured data is created. This measured data is compared with theoretical data generated based on a theoretical set of parameters as applied to a model representing the physical structure of the semiconductor. The model includes an interface layer, between the film layer and the silicon substrate, which includes a representation of the electronic structure of the underlying substrate. In the preferred embodiment, the representation is a five peak, critical point model influenced by the electronic transitions of the underlying silicon substrate. An error minimization algorithm, such as a least squares fitting routine, is used to modify the theoretical parameters until the differences between the measured data and the theoretically derived data is minimized.

30 Claims, 8 Drawing Sheets

ANALYSIS OF INTERFACE LAYER CHARACTERISTICS

PRIORITY

This application claims priority from prior provisional application Ser. No. 60/189,744 filed Mar. 16, 2000 and Ser. No. 60/266,912, filed Feb. 7, 2001.

TECHNICAL FIELD

The subject invention relates to measurements of thin films on semiconductor wafers. More particularly, the invention relates to a new approach for analyzing and characterizing the interface layer between the thin film and the substrate in order to more accurately determine the characteristics of the sample.

BACKGROUND OF THE INVENTION

Various optical metrology devices have been developed for measuring and characterizing thin films on semiconductor wafers. One such tool is described in PCT application WO/9902970, published Jan. 21, 1999. The assignee herein has commercialized the device described in that patent application under the name OPTI-PROBE 5240. This device includes a number of measurement technologies. More specifically, the device includes a beam profile ellipsometer (BPE) (see U.S. Pat. No. 5,181,080); a beam profile reflectometer (BPR) (see U.S. Pat. No. 4,999,014); relatively conventional broad band (BB) and deep ultraviolet (DUV) spectrometers; a proprietary broad band spectroscopic ellipsometer (SE) (see U.S. Pat. No. 5,877,859) and an off-axis narrow band ellipsometer (see U.S. Pat. No. 5,798,837). All of the above-recited patents and PCT applications are incorporated herein by reference.

In order to evaluate a sample based on the measurements taken by the technologies mentioned above, various types of fitting algorithms have been developed. These algorithms start with a model of the expected structure of the test sample. In a simple case, the sample might be a silicon substrate covered with a thin layer of silicon oxide. The algorithm is seeded with information about expected parameters of the two materials such as the thickness, extinction coefficient and index of refraction. Using the Fresnel equations, the algorithm calculates expected measurement values, i.e. what data would be measured by the selected optical technique assuming the original guess of the expected sample parameters was correct. These calculated expected measurements are then compared with the actual measurements obtained with the device. Any differences between the calculated measurements and the actual measurements is an indication that the original guesses of the sample parameters were incorrect. Based on the amount of deviation between the theoretical measurements and the actual measurements, the algorithm will adjust the theoretical parameters of the sample (i.e. change the "guess" of the thickness of the oxide layer) and perform another calculation to determine expected measurement values. This process is repeated in an iterative fashion until the calculated measurement values closely match the actual measured values. At this point, it is assumed that the parameters used to generate the expected measurement values are reasonably close to the actual parameters of the sample. Further details about the use of such fitting algorithms can be found in "Simultaneous Measurement of Six Layers in a Silicon on Insulator Film Stack Using Spectrophotometry and Beam Profile Reflectometry," Leng et. Al, Journal of Applied Physics, Vol. 81, No. 8, Apr. 15, 1997, page 3570–3578.

In order for this approach to be accurate, it is important that the model selected correspond quite closely to the structure of the actual sample. Each layer in the model is assumed to have certain unique characteristics. In the situation described above, where a thin film oxide layer is deposited on a substrate, it would be acceptable to create a model which accounted for only those two different materials, provided that the thin film layer was relatively thick, i.e. a few hundred angstroms or more. However, this simple modeling approach is not acceptable for much thinner layers. This is because the region between the substrate and the thin film layer defines an interface region which has characteristics somewhat different from either the substrate or the thin film layer. This interface region can be about 5 to 10 angstroms thick and contributes to the sample's response to reflected light. When measuring relatively thin films, on the order of 30 angstroms or less, which is typical thickness of gate oxides used in current state of the art lithography processes, one cannot ignore the presence of the interface layer in creating the theoretical model for analyzing the data.

The need to model the interface layer has been discussed in the past. In the prior art, it was assumed that the interface layer had characteristics similar to the thin film layer. Most researchers treated the interface layer as having essentially the characteristics of the thin film layer, but with a higher refractive index. While this approach has helped to improve accuracy of the modeling over situations where no interface layer is considered, the results have been inadequate for accurately measuring the thinnest of the thin films. In other approaches, the interface layer was treated as having a blend of characteristics from the thin film layer and substrate. The latter approaches did not include representations of the specific electronic structure of the underlying silicon.

Accordingly, it is an object of the subject invention to provide a new modeling approach which significantly improves the analysis of data and provides more accurate measurement results for thin films.

SUMMARY OF THE INVENTION

It has been recognized by the inventors herein that the characteristics of the interface layer should be expanded to include the electronic characteristics of the underlying substrate. Accordingly, when a model is created to analyze samples, particularly in very thin film situations, the interface layer should be characterized as being a combination of the characteristics of the underlying substrate and the thin film.

In the preferred embodiment, applicants believe that the critical point models developed in the past to characterize the interaction between silicon and light are best suited for this approach. As described herein, a five-peak critical point model was used for analyzing test data. The five-peak critical point model is used to help characterize the refractive index and extinction coefficient of the interface layer. It was found that when these modifications were made to the modeling of the interface layer, far more accurate results were achieved in measuring the characteristics of the thin film on the semiconductor.

The invention is carried out as part of the analysis of the data obtained from one or more measurement techniques. More particularly, a theoretical model is set up which includes the substrate, the thin film layer and an interface layer. The interface layer is characterized as having parameters corresponding to both the thin film and the underlying substrate. This model is then used in conjunction with the Fresnel equations to calculate expected measurement data.

This theoretical calculated data is then compared to the actual measured data. Differences between the calculated data and the actual measured data are then used to vary the expected characteristics of the sample in an iterative process for determining the actual composition of the sample.

In the examples set forth below, a variety of silicon samples having thermal oxides deposited thereon were measured using a rotating compensator spectroscopic ellipsometer. The results of the new modeling approach demonstrated a high degree of accuracy. It is believed that this approach can be used to analyze a variety of multilayer structures including silicon oxide on silicon as well as other thin films and substrates. It is believed this approach is particularly useful for materials with high extinction coefficients such as hafnium oxide and zirconium oxide. This approach can also be used to model the interface between a dielectric layer and a substrate.

It should be noted that even though this invention relates to modeling an interface layer between a substrate and the adjacent layer, this approach can be applied to multilayer structures. In particular, a model for a three layer sample would include the substrate, the three individual layers and the interface layer between the substrate and the lowermost layer. Examples of such multilayer structures include oxide-nitride-oxide (ONO), oxide-poly-oxide (OPO) and barium-strontium-titanate (BST).

In the examples discussed below, the data was obtained from a spectroscopic rotating compensator ellipsometer. It should be understood that the subject modeling approach is not limited to the type of tool used to obtain the optical measurements. The model is used to predict what the measurement response to the interface layer would be for any type of optical metrology tool, including but not limited to those of the type described in PCT WO/9902970 cited above.

It should also be noted that past attempts to model the interface included effective medium modeling. In these approaches, some general blend of characteristics were used. These approaches did not preserve the actual physical and electronic structure and transitions of the silicon.

In the method of the subject invention, the modeling includes creating dispersion curves of the interface layer that include the electronic transitions of silicon. This can include one or more of the critical points discussed in the attached articles.

Further objects and advantages of the subject invention can be understood from the following detailed description of the modeling and experimental results.

DETAILED DESCRIPTION OF THE PREFERRED EMBODIMENTS

Analytic representations of the dielectric responses of semiconductors have been reported in the literature for c-Si, a-Si and c-Ge (See, J. Leng, J. Opsal, H. Chu, M. Senko, and D. E. Aspnes, Thin Solid Films, 313 (1998) 132 and J. Leng, J. Opsal, H. Chu, M. Senko, and D. E. Aspnes, J. Vac. Sci. Technol., A 16 (1998) 1654). They are more convenient than tabular data for analyzing complex materials and structures by optical methods. In addition, the information obtained by studying c-Si forms the basis for more complex materials such as silicon oxynitrides (SiON) and silicon/silicon dioxide interfaces. The real $\epsilon_1$ and imaginary $\epsilon_2$ parts of the dielectric function can be expressed as $\epsilon=\epsilon_1+i\epsilon_2$ of any semiconductor (see for example, D. E. Aspnes, W. E. Quinn, M. C. Tamargo, M. A. A. Pudensi, S. A. Schwarz, M. J. S. P. Brasil, R. E. Nahory, and S. Gregory, Appl. Phys. Lett., 60 (1992) 1244.)

Here, we investigate analytic representations for the dielectric responses of c-Si and c-Si/$SiO_2$ interface. We will try to assign each peak to the physical transitions of the band structure of the c-Si. Using the basis of the five peaks from the c-Si, we will develop the c-Si/$SiO_2$ interface model in the same context of five peaks.

Analytic Representations

The dielectric function can be expressed in an extended harmonic oscillator model as described in C. C. Kim, J. W. Garland, H. Abad, and P. M. Raccah, Phys. Rev., B45 (1992) 11749 and F. L. Terry Jr., J. Appl. Phys., 70 (1991) 409:

$$\varepsilon(\omega) = \varepsilon_0 \sum_j F_j/2 e^{i\pi S_j}[1/(1-\omega/E_j - i\Gamma_j) + 1/(1+\omega/E_j + i\Gamma_j)].$$

The real oscillator strength $F_j$ is replaced by a complex oscillator strength with a phase $S_j$. We refer to this as the critical point (CP) model. The phase factor stems from the electron-electron and other interactions. The CP model is analytic and satisfies the Kramers-Kronig relations. Since the imaginary part of the CP model is asymmetric relative to the energy, it is quite flexible for fitting general line-shapes.

Applications

We investigate the capability of the above expression to represent $\epsilon$ spectra by applying them to the tabulated standard references for c-Si (See T. Yasuda and D. E. Aspnes, Appl. Opt., 33 (1994) 7435).

We used five peaks to describe the c-Si. Since each peak needs 4 parameters (F, S, E, Γ), the total number of parameters are 21 (including the constant $\epsilon_0$).

The parameters for the CP model are

| CP(Si) | F | E | Γ | S |
|---|---|---|---|---|
| 1 | 1.84943 | 3.37394 | 0.037312 | −0.234323 |
| 2 | 5.87886 | 3.75058 | 0.145069 | −0.134146 |
| 3 | 2.75095 | 4.26748 | 0.046885 | 0.03755098 |
| 4 | 10.5313 | 4.65649 | 1.51991 | 0.318381 |
| 5 | 0.37586 | 5.23844 | 0.060917 | −0.147449 | and $\epsilon_0 = 0.950139$.

Figure 1:
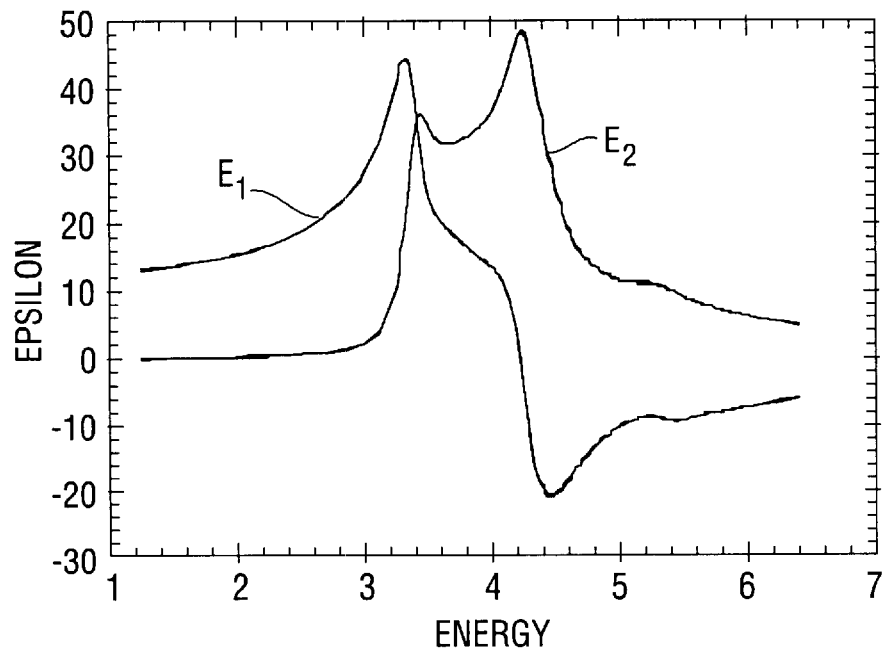
FIG. 1 is a graph of the dielectric function of c-Si.

As seen in FIG. 1, there are three relatively sharp peaks in the spectrum of $\epsilon_2$: peak 1 at 3.37 eV with Γ of 0.037 eV, peak 2 at 4.27 eV with Γ of 0.047 eV, and peak 3 at 5.24 eV with Γ of 0.061 eV. Two additional broad peaks are found at 3.75 eV with Γ of 0.145 eV and at 4.66 eV with Γ of 1.52 eV.

The assignments of these three sharp peaks are well-established (see M. L. Cohen and J. R. Chelikowsky, in Electronic Structure and Optical Properties of Semiconductors, Springer-Verlag, Berlin, 1988). The first peak comes from the direct transition in Γ and L point of the Brillouin zone. In the case of Si, the band structure is approximately two-dimensional along the (111) direction, therefore the contribution to peak 1 is almost degenerate from Γ and L point. It is generally denoted as ($E_o'$, $E_1$) for peak 1 at 3.37 eV. The second sharp peak at 4.27 eV is denoted as $E_2$. This structure arises from large regions of the Brillouin zone, most notably around the special point $(2\pi/a)(¾, ¼, ¼)$ (a is the lattice constant). The highest peak at 5.24 eV is denoted by $E_1'$. This peak occurs near the L point and along the Λ direction.

Next we apply the same model to the Si/SiO$_2$ interface. The parameters for the CP model are:

| CP(Si/SiO$_2$) | F | E | Γ | S |
|---|---|---|---|---|
| 1 | 2.91003 | 3.53411 | 0.100456 | 0.199662 |
| 2 | 14.0015 | 3.92347 | 0.243772 | −0.389039 |
| 3 | 5.0604 | 4.50865 | 0.149516 | 0.631771 |
| 4 | 2.35152 | 5.54606 | 0.286906 | 0.416655 |
| 5 | 19.9944 | 8.73172 | 2.05967 | 0.608526 | with $\epsilon_0 = 0.500472$.

Figure 2:
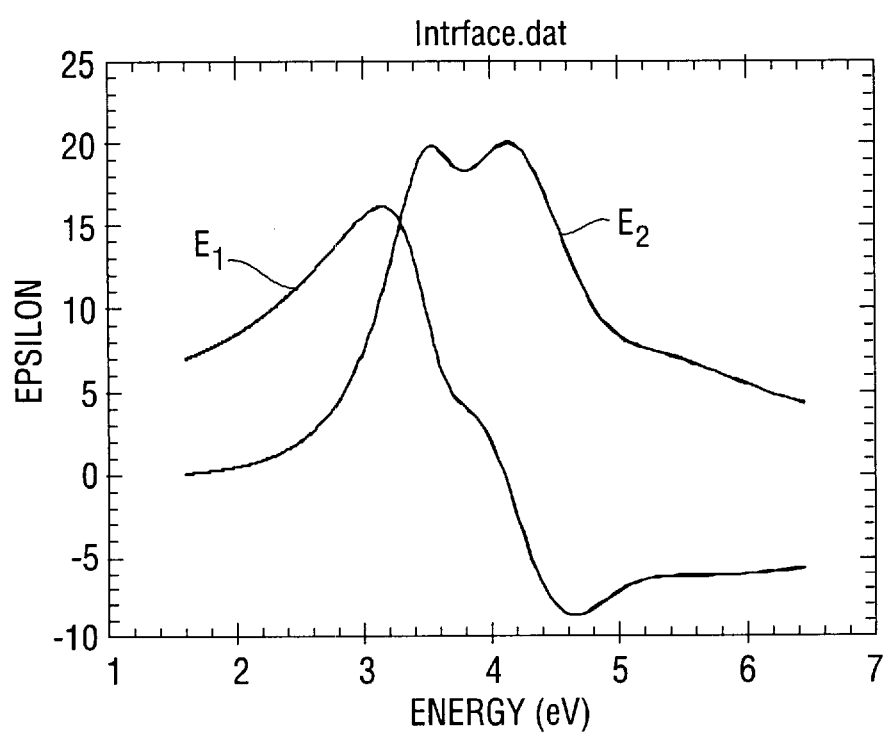
FIG. 2 is a graph of the dielectric function of an $SiO_2$ interface.

As seen in FIG. 2, the Si/SiO$_2$ interface in general retained the three features that observed in c-Si: the first peak of ($E_0'$, $E_1$) with peak position shifted to higher energy at 3.53 eV with a broadened linewidth Γ=0.10 eV. The second peak of $E_2$ is upper shifted to 4.51 eV with a broadened linewidth of 0.15 eV. The third peak of $E_1'$ is shifted to 5.55 eV with a broadened linewidth of 0.29 eV. The other two broad peaks are at 3.92 eV and 8.73 eV compared to 3.75 eV and 4.66 eV in c-Si.

Discussion

We found that the both c-Si and Si/SiO$_2$ interface can be represented by a five peak CP model. The physical meaning of the three obvious peaks in $\epsilon_2$ spectra of c-Si were assigned as optical transitions in the context of the electronic structures of c-Si. We found that the interface of Si/SiO$_2$ resembles that of the c-Si except that the peaks of $\epsilon_2$ are less prominent and the features are broadened. This is in line with the generally accepted view that the interface of Si and SiO$_2$ should be a gradual transition from amorphous Sio$_2$ to the crystalline Si.

EXAMPLES

Example No. 1

Rotating compensator spectroscopic ellipsometry (RCSE) from 195–915 nm has been used to study the interface between c-Si and several thermal oxides with a variety of origins. (The RCSE which we used is described in U.S. Pat. No. 5,877,859 cited above). The first set of two wafers was obtained from NIST with 15 and 24 Å of thermal PATENT oxide on a (001) c-Si surface. Another set, taken from Therma-Wave standards, consisted of ten (001) c-Si wafers with thermal oxide thicknesses ranging from 10 to 9000 Å. The final wafer consisted of 20 Å of thermal oxide on a (111) c-Si surface. It is known that fresh thermal oxide surfaces accumulate a thin 3–5 Å layer over a period of one week, which complicates the characterization of the interface layer between thermal oxide and c-Si. We used a prototype desorber to remove the accumulation layer prior to all measurements. All data suggest an interface layer of 7–9 Å between the thermal oxides and the c-Si. We have also used RCSE to characterize the dispersion of the interface layer. Using a five-peak critical point (CP) model, we found that the dielectric response of the interface layer resembles that of a mixture of thermal oxide and c-Si. When this interface layer was included in the model, the total residual of the model fitting to the RCSE data improved by a factor of two. Data obtained on the same set of TWI standard wafers with our bench RCSE and a SOPRA rotating polarizer ellipsometry (RPE) model GESP over their common accessible wavelength ranges are compared and found to be in agreement within 5 Å.

SiO$_2$/Si interface is of most importance to the modern integrated circuits (IC) industry. Many studies with single wavelength null ellipsometry, rotating analyzer ellipsometry (RAE), or polarization modulation ellipsometry (PME) have pointed out that the SiO$_2$/Si interface is on the order of 6–10 Å with an index of 2.8. However, none of the above studies involve gate oxide overlayer of thickness less than 30 Å, which becomes the upper limit for the gate oxide requirement for the 130 nm lithograph process. RCSE has many advantages over RAE since it contains the unique sinΔ information in the sin2wt Fourier component in addition to the traditional cosΔ and tanψ that are also obtained from sin4ωt and cos4ωt Fourier components (See J. Opsal, J. Fanton, J. Chen, J. Leng, L. Wei, C. Uhrich, M. Senko, C. Zaiser, and D. E. Aspnes, Thin Solid Films 313–314, 58 (1998)). In the application of a thin dielectric film on c-Si, the phase shift A caused by the thin film is close to 180° where the measurement of cosΔ loses its sensitivity and that of sinΔ become linearly proportional to film thickness t. We report in this work measurements of ultrathin gate oxides (<30 Å) by RCSE. We used a critical point model to represent the interface between the oxide and Si. Such a model was used throughout the study with oxide film thickness ranging from 10–9000 Å.

Experimental

A research grade bench top RCSE was built with tungsten and deuterium lamp light sources. The angle of incidence of the light beam can be have one of the values: 45°, 65°, and 70°. The polarizer and analyzer azimuthal angles are set at 45° and −45°, respectively. The wavelength range of the bench top RCSE is from 195–915 nm. A Sopra RPE model GESP was used in comparison with our bench top RCSE. The Sopra SE wavelength range is from 300–800 nm. A prototype desorber was used to remove the accumulated overlayer by heating the wafer up to 300° C. for 5 min before the SE measurement.

Results

Figure 3:
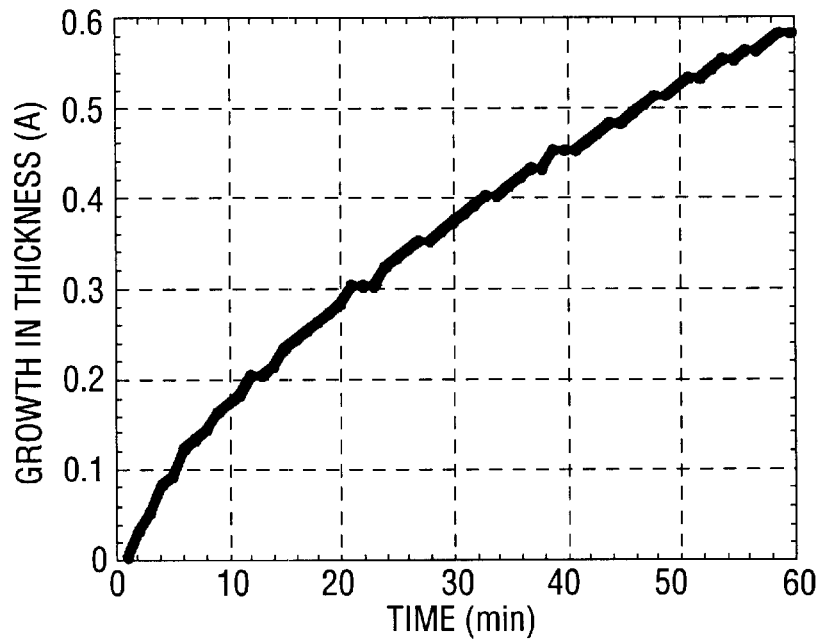
FIG. 3 is a graph of overlayer thickness growth under air atmosphere in a class 10 clean room environment as a function of time.

Desorber: It is well known that the overlayer of oxide can grow under the atmosphere of air. The growth rate can be from 3–5 Å in a time period of one to two weeks depending on the condition of the clean room. FIG. 3 is a plot of the growth of the overlayer in a class 10 clean room environment right after the wafer was desorbed for 5 min at 300° C. The overlayer growth rate is about 0.6 Å in a one hour period. Since the oxide film thickness of this wafer is 24 Å, the grown layer is a significant portion of the total thickness when the sample was exposed to air over several days. To avoid the measurement errors caused by the grown layer a desorber was used to remove it before the SE measurement.

Dispersions: We used published data for thermal oxide and c-Si (See, I. H.

Malitson, J. Opt. Soc. Am. Vol. 55, 1205 (1965) and T. Yasuda and D. E. Aspnes, Appl. Opt. 33, 7435 (1994). For the $SiO_2/Si$ interface, we used a five-peak critical point (CP) model. A typical dispersion is plotted in FIG. 4.

Figure 5A:
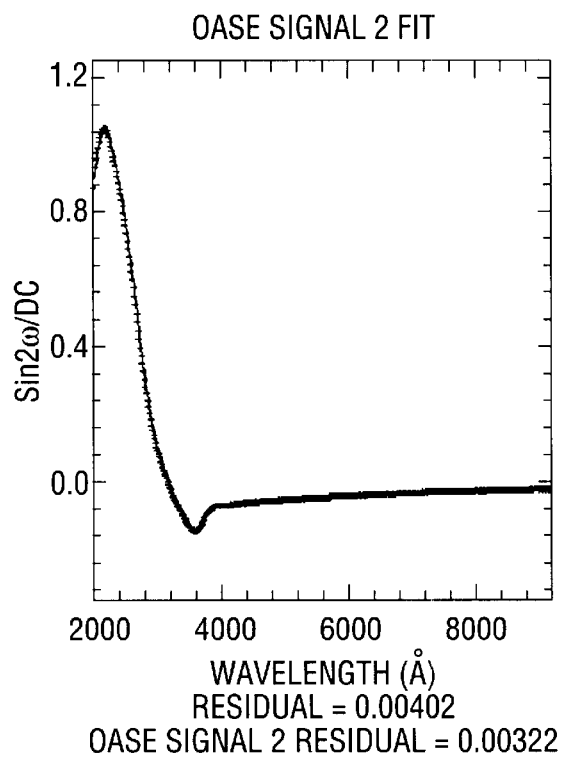
FIGS. 5a, 5b and 5c illustrate fitting to Fourier coefficients data from an RCSE for a NIST wafer with thickness nominal value of 15 Å.
Figure 5B:
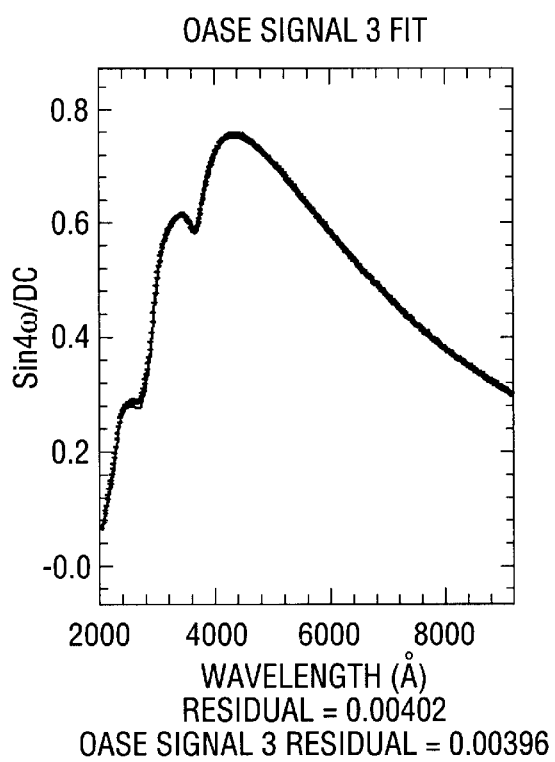
Figure 5C:
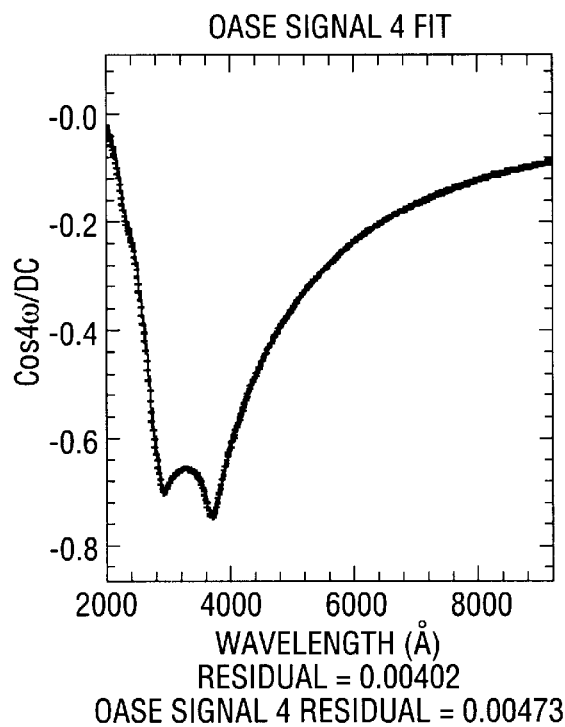

NIST Wafers: FIGS. 5a to 5c show the RCSE data taken at an incident angle of 70° along with the best fit using a Levenberg-Marquardt algorithm. The model used in FIGS. 5a to 5c is $SiO_2/Si$. The best fit to the data gives the thickness of 17 Å and the residual of $4 \times 10^{-3}$.

Figure 4:
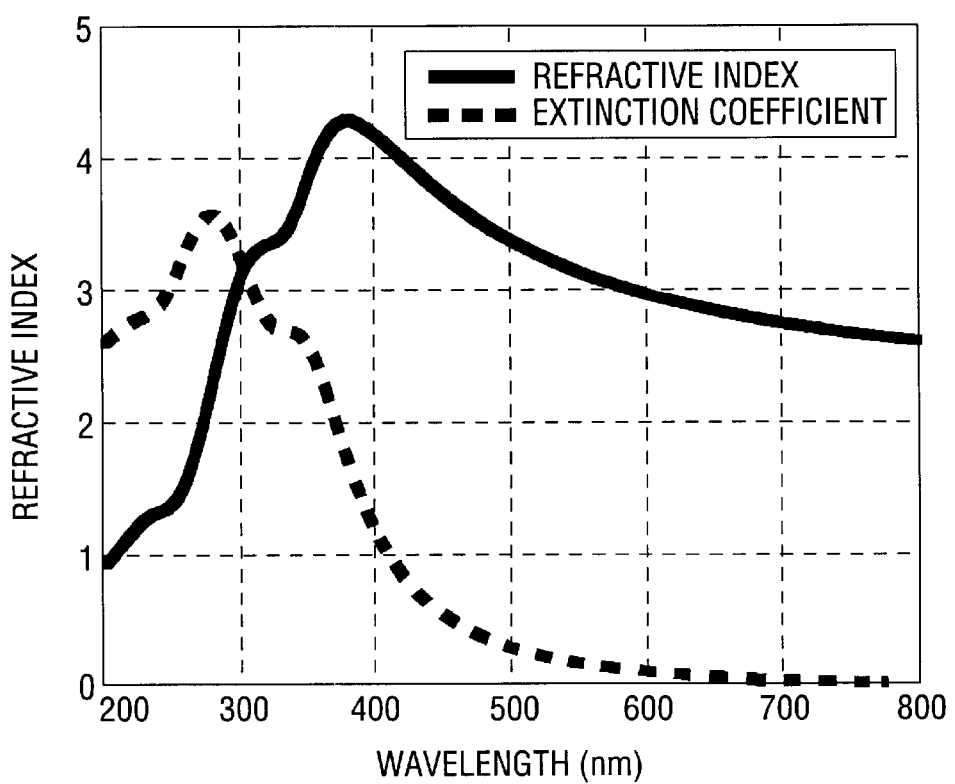
FIG. 4 is a graph of the refractive index and extinction coefficient of a $SiO_2/Si$ (001) interface layer modeled with a 5-peak critical point representation for the NIST wafers.

However, when the interface layer is included in the model with the dispersion plotted in FIG. 4, the thicknesses of the $Sio_2$ film and the interface layer are 11 and 9 Å, respectively and the residual decreased to $2 \times 10^{-3}$. Similar results were obtained for the other NIST wafer of nominal value of 24 Å. The results are summarized below:

TABLE I

Results of RCSE measurement of NIST wafers with and without interlayer models. The surface orientation is (001).

| Wafer # | $SiO_2/Si$ | Residual | $SiO_2$/interlayer/Si | Residual |
|---------|------------|----------|-----------------------|----------|
| 1 | 17 Å | 4 × 10 − 3 | 11 Å/9 Å | 2 × 10 − 3 |
| 2 | 26 Å | 4 × 10 − 3 | 20 Å/9 Å | 2 × 10 − 3 |

Therma-Wave Standard Wafers: The TWI standard set consists of ten wafers of six inch in diameter with $SiO_2$ film on Si (001) surface. The results of the best fit to the bench top RCSE data are listed in Table II.

TABLE II

Results of RCSE measurements of TWI wafer set with and without interface layer.

| Wafer # | $SiO_2/Si$ (Å) | Residual (10 − 3) | $SiO_2$/Interface (Å) | Residual (10 − 3) |
|---------|----------------|-------------------|------------------------|-------------------|
| 1  | 14   | 3.2  | 8/7     | 1.9  |
| 2  | 75   | 3.3  | 68/8    | 2.0  |
| 3  | 204  | 3.5  | 197/8   | 2.1  |
| 4  | 470  | 5.2  | 463/6   | 3.5  |
| 5  | 967  | 9.5  | 963/4   | 8.4  |
| 6  | 2091 | 10.0 | 2087/4  | 9.3  |
| 7  | 4223 | 14.4 | 4217/10 | 13.4 |
| 8  | 5964 | 18.8 | 5959/10 | 17.8 |
| 9  | 7479 | 21.4 | 7472/12 | 20.1 |
| 10 | 9150 | 23.8 | 9142/14 | 22.5 |

The same set of wafers was measured with a SOPRA RPE model GESP. The same dispersion of the interface was also used for the data analysis. The results are listed in Table III.

TABLE III

Results of SOPRA RPSE GESP measurements of TWI wafer set with and without interface layer.

| Wafer # | $SiO_2/Si$ (Å) | Residual (10 − 3) | $SiO_2$/Interface (Å) | Residual (10 − 3) |
|---------|----------------|-------------------|------------------------|-------------------|
| 1  | 12   | 8.1  | 5/8     | 7.6  |
| 2  | 70   | 9.5  | 65/6    | 9.5  |
| 3  | 202  | 4.6  | 199/4   | 4.5  |
| 4  | 468  | 4.1  | 463/7   | 3.7  |
| 5  | 965  | 9.9  | 965/0   | 9.9  |
| 6  | 2086 | 11.7 | 2082/7  | 11.4 |
| 7  | 4220 | 10.2 | 4213/10 | 9.1  |
| 8  | 5950 | 12.7 | 5940/17 | 10.7 |
| 9  | 7470 | 13.9 | 7460/16 | 12.4 |
| 10 | 9145 | 16.2 | 9134/17 | 14.4 |

We note that the fitting wavelength range is 195–915 nm and 300–800 nm for results listed in Table II and III, respectively. If the same wavelength range of 300–800 nm was used in both cases, the residuals for wafer 7–10 in Table II will be consistently lower than that in Table III.

Figure 6:
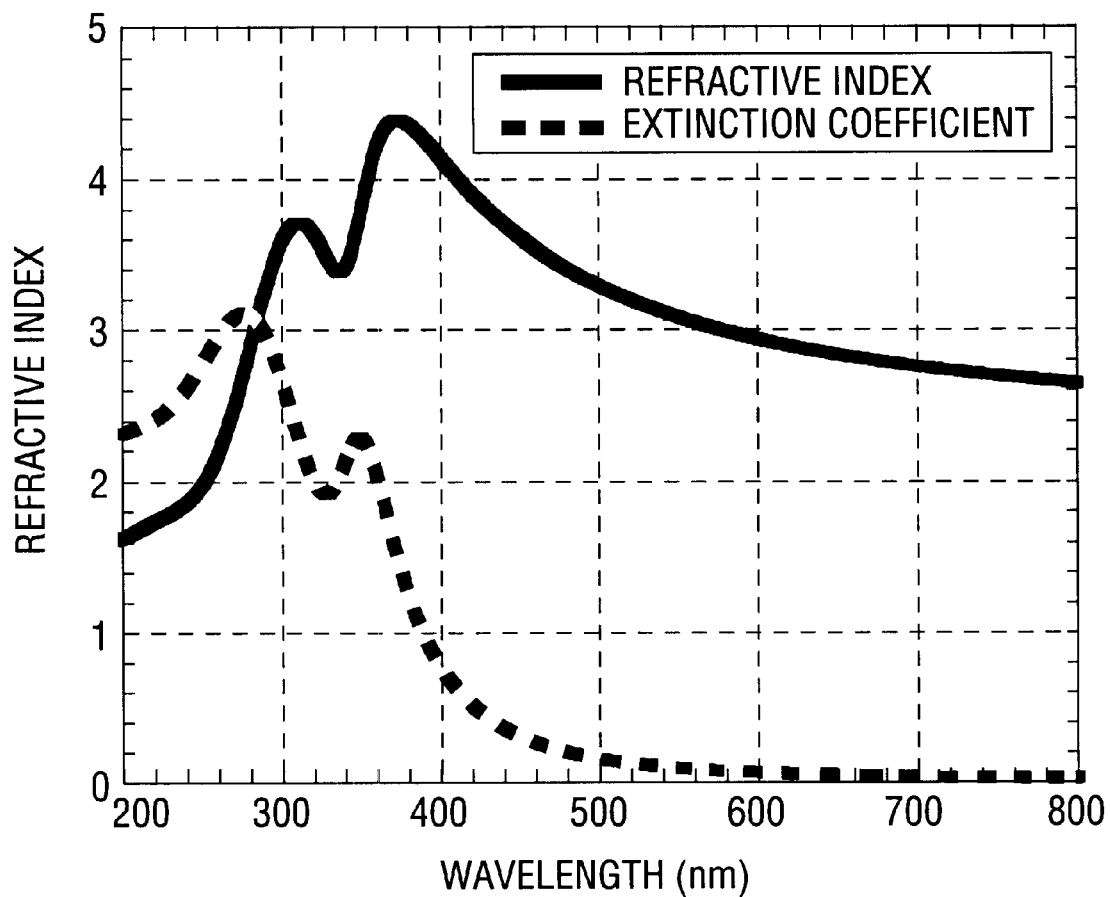
FIG. 6 is a graph illustrating the refractive index and extinction coefficient of the interface layer modeled for an SiO2 thin film on a Si (111) surface.

$SiO_2$ thin film on a Si (111) surface: The results of fitting to the RCSE data are listed in Table IV. The model used the dispersion plotted in FIG. 6.

TABLE IV

Results of RCSE measurements of $SiO_2$ on a Si (111) surface with and without the interface layer.

| Wafer # | $SiO_2/Si$ | Residual | $SiO_2$/interlayer/Si | Residual |
|---------|-----------|----------|------------------------|----------|
| 1 | 20 Å | 3.5 × 10 − 3 | 16 Å/4 Å | 2.5 × 10 − 3 |

Conclusions for Example 1

We have measured three sets of $SiO_2$ wafers that were prepared under different conditions with RCSE, namely, two thin oxide (001) wafers from NIST, one set of (001) wafers from TWI standards, and one thin oxide on a Si (111) surface. In all three cases there exists an interlayer between the $SiO_2$ and Si substrate. The interlayer was modeled using a five-peak critical point representation. For thin $SiO_2$ films (<200 Å) on Si (001) surface, the interlayer is on the order of 7–9 Å, i.e., roughly 2–3 monolayer thick. For a thin film $SiO_2$ film on a Si (111) surface, the interface layer is on the order of 4 Å, or roughly one monolayer thick. The thickness measured by RCSE agrees with SOPRA GESP within 5 Å.

Example 2

High-k dielectric materials are essential for next-generation gate-dielectric applications. $HfO_2$ is a promising high-k dielectric with a dielectric constant of 30 and an energy gap of 5.68 eV. The interface layer between $HfO_2$ and c-Si plays an important role in the quality of Si devices as evidenced by electrical measurements. Noninvasive methods of determining the thickness of the interface region are therefore highly desirable to ensure device quality. We report here an investigation of the interface between $HfO_2$ and c-Si using a rotating-compensator spectroscopic ellipsometer that operates from 200 to 800 nm. Samples were prepared by a dc magnetron-reactive sputtering method and subsequently furnace annealed at temperatures ranging from 500 to 850° C. Thicknesses of the $HfO_2$ layers varied from 35 to 180 Å. Interface layers 7 to 20 Å thick were found in all cases depending on annealing conditions and the thicknesses of the HfO$_2$ films. Transmission electron micrographs confirm the RCSE results, indicating that RCSE can be used as an effective in-fab monitoring tool for device quality control.

High-k dielectric materials such as Ta$_2$O$_5$, TiO$_2$, SrTiO$_3$, and BaSrTiO$_3$ have received much recent attention as a result of the interest shown in the use of high-dielectric-constant materials for gate dielectrics. However, these are thermally unstable when contacting silicon directly and need an additional barrier layer, which modifies the electrical properties of the interface. Hafnium oxide, HfO$_2$, on the other hand, has a high dielectric constant and good thermal stability when forming an interface with Si. In electrical measurements, the leakage current and breakdown voltage depend not only on the thickness of the HfO$_2$ layer but also on the thickness of the interface between the HfO$_2$ layer and the c-Si substrate. In the range of equivalent oxide thickness (EOT) that can be deduced from the physical thickness and static dielectric constant of ~30 of HfO$_2$, the leakage current of ultrathin HfO$_2$ films of thicknesses less than 30 Å is less than that of SiO$_2$ thin films. When the physical thickness of the HfO$_2$ layer approaches zero and the EOT approaches the thickness of the interface, the leakage current increases dramatically, demonstrating the importance of controlling and reducing the thickness of the interface layer. Here, we report an investigation of HfO$_2$ thin films and their interfaces with c-Si as measured by a rotating-compensator spectroscopic ellipsometer (RCSE). The samples are HfO$_2$ films with thickness ranging from 35 to 180 Å and annealed at various temperatures. With the proper modeling of the dispersions of HfO$_2$ and its interface with c-Si, the thicknesses of the HfO$_2$ film and the interface layer can be determined simultaneously. The results obtained from RCSE are in good agreement with those obtained by transmission electron microscopy (TEM).

Experimental

HfO$_2$ was deposited directly on p-type silicon substrates using a reactive dc magnetron sputtering method. During sputtering the oxygen flow was modulated to control the growth and quality of the interface layer. When the process was properly controlled, the dielectric constant of HfO$_2$ approached 28 and the thickness of interfacial layer was reduced to ~6 Å. The samples were annealed with N$_2$ purging up to 700° C. The RCSE overcomes the limitations of the more common rotating-analyzer ellipsometer (RAE) configuration when applied to ultrathin dielectric films on c-Si substrates. Details of our RCSE are given at J. Opsal, J. Fanton, J. Chen, J. Leng, L. Wei, C. Uhrich, M. Senko, C. Zaiser, and D. E. Aspnes, Thin Solid Films 313–314, 58 (1998). In brief, the angle of incidence is 70° and the polarizer and analyzer angles are 45° and −45°, respectively. The instrument covers the wavelength range of 200 to 800 nm. In particular, with the compensator rotating at an angular frequency of $\omega$, a sin2$\omega$wt Fourier component is generated in the output that for thin dielectric films is directly proportional to the film thickness through the measured phase shift $\Delta$.

Results

Figure 7A:
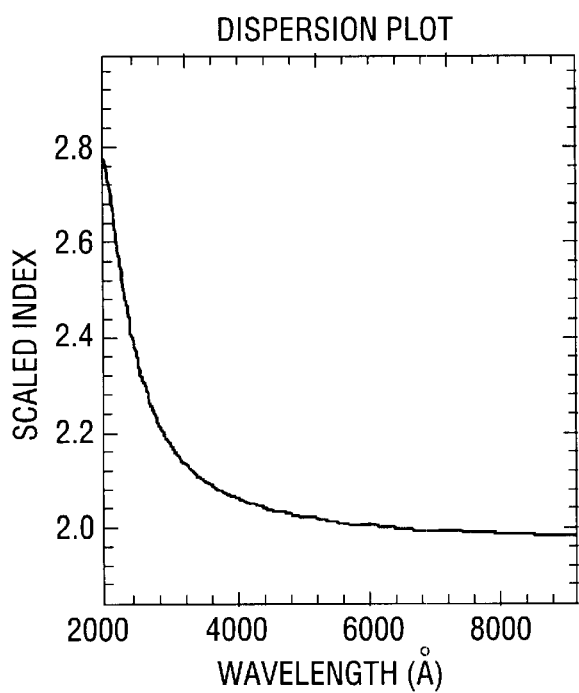
FIGS. 7a and 7b are graphs illustrating the refractive index and extinction coefficient of $HfO_2$.
Figure 7B:
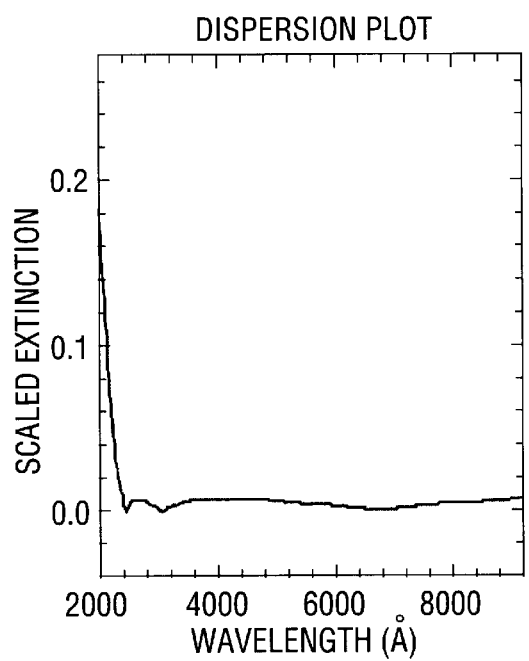

The optical properties of HfO$_2$ films of thicknesses from 500 to 10000 Å have been reported in the literature (See, M. Fadel, O. A. Azim, O. A. Omer, R. R. Basily, Appl. Phys. A. 66, 335 (1998)). The refractive index n of HfO$_2$ is essentially flat, being nearly equal to 2.0 from 350 to 1900 nm. Its extinction coefficient k indicates a weak absorption, less than 0.025, from 350 to 500 nm. However, no dispersion data are available below 350 nm. We used a Cauchy model to describe the dispersion of HfO$_2$ from 200 to 800 nm. The result is illustrated in FIGS. 7a and 7b. To our level of sensitivity the extinction coefficient of HfO$_2$ is zero for films 30 to 150 Å thick.

Figure 8A:
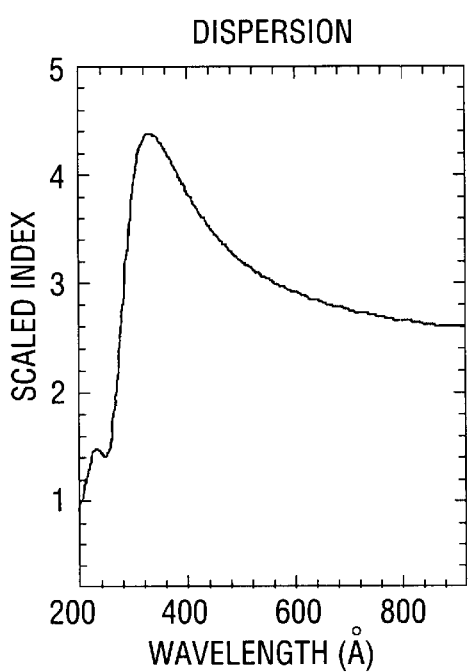
FIGS. 8a and 8b illustrate the dispersion of the hafnium silicate interface between $HfO_2$ and c-Si.
Figure 8B:
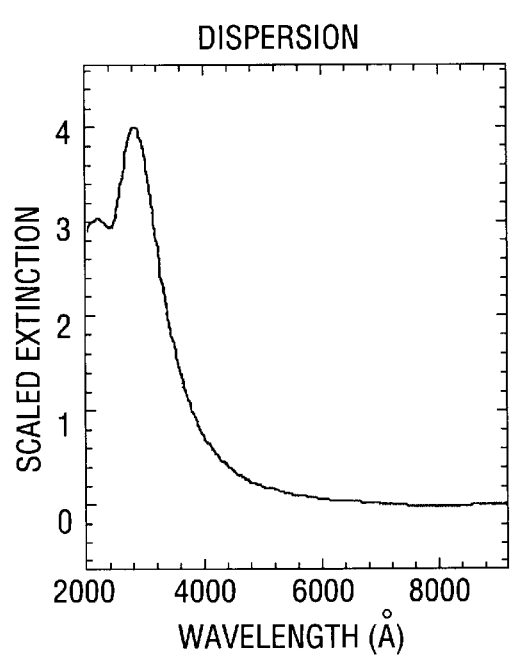

We described the dispersion of the hafnium silicate interface between HfO$_2$ and c-Si by a critical point (CP) model. The dispersion of this interface is shown in FIGS. 8a and 8b.

Figure 9A:
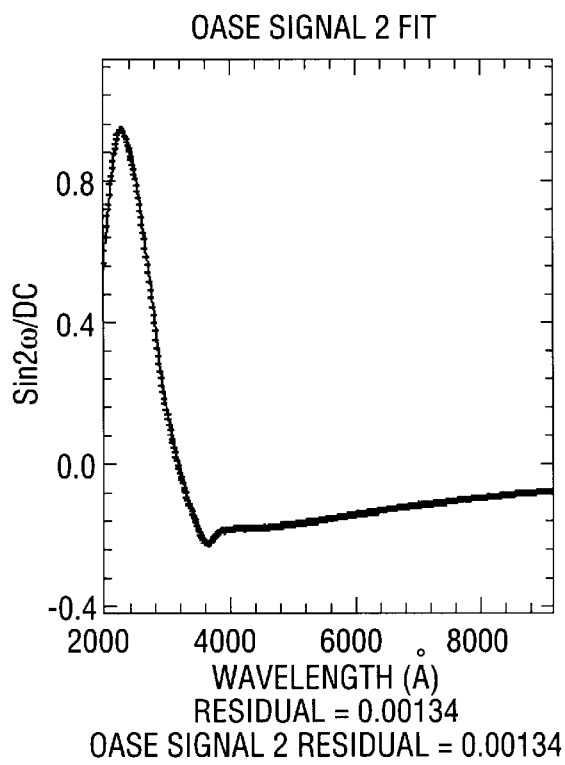
FIGS. 9a, 9b and 9c are RCSE data and fitted curves for sin2ω, sin4ω, and cos4ω Fourier coefficients.
Figure 9B:
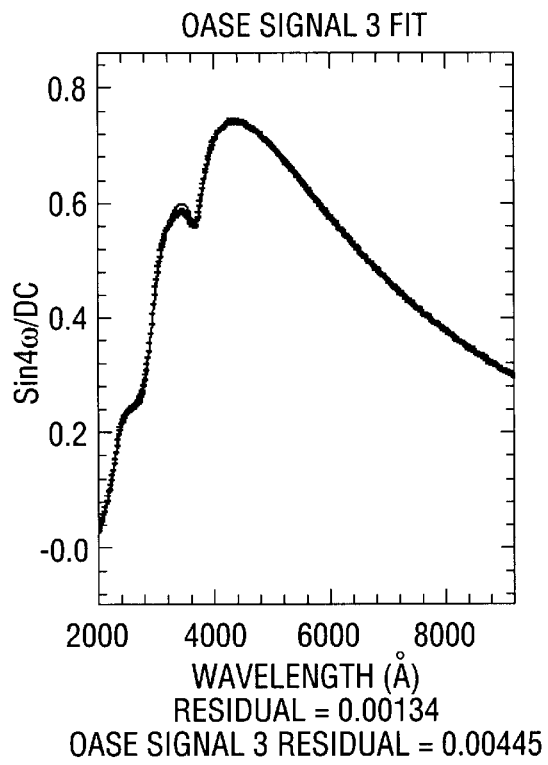
Figure 9C:
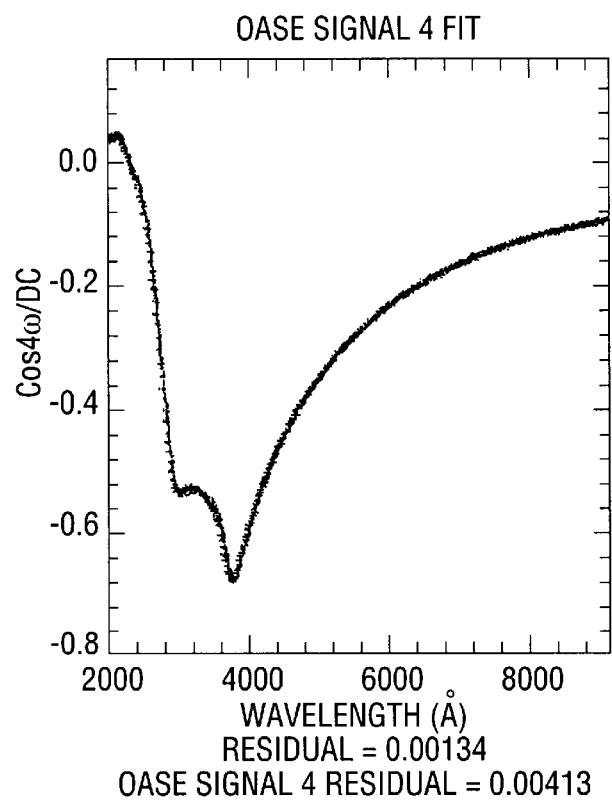
Figure 10A:
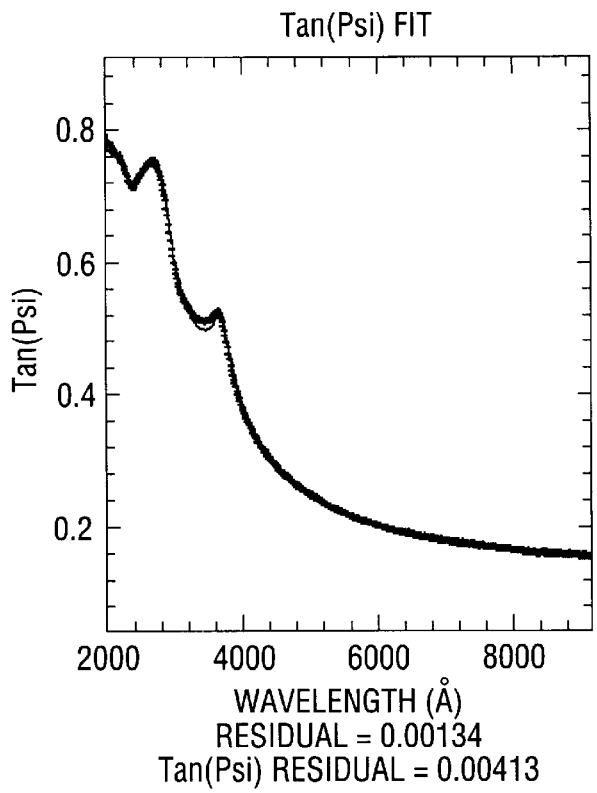
FIGS. 10a and 10b represent best fits to tanψ and cosΔ. The data are plotted as crosses and the fit as lines.
Figure 10B:
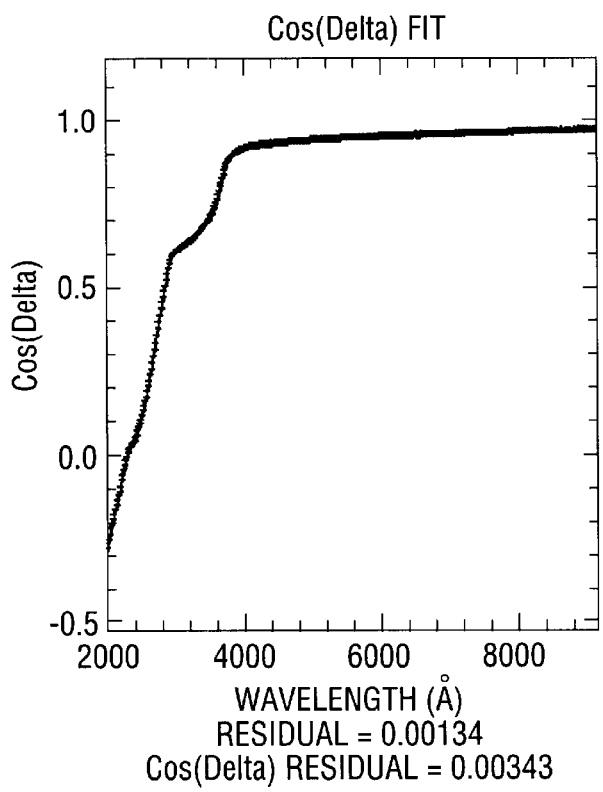

A typical best fit to the RCSE sin2$\omega$, sin4$\omega$w, and cos4$\omega$ Fourier coefficients is shown in FIGS. 9a–c The Fourier coefficient of cos2w is zero, according to theory and verified by experiment. We can also express the Fourier coefficients in terms of tan$\psi$ and cos$\Delta$. The best fit to the data is shown in FIGS. 10a and 10b.

Figure 11:
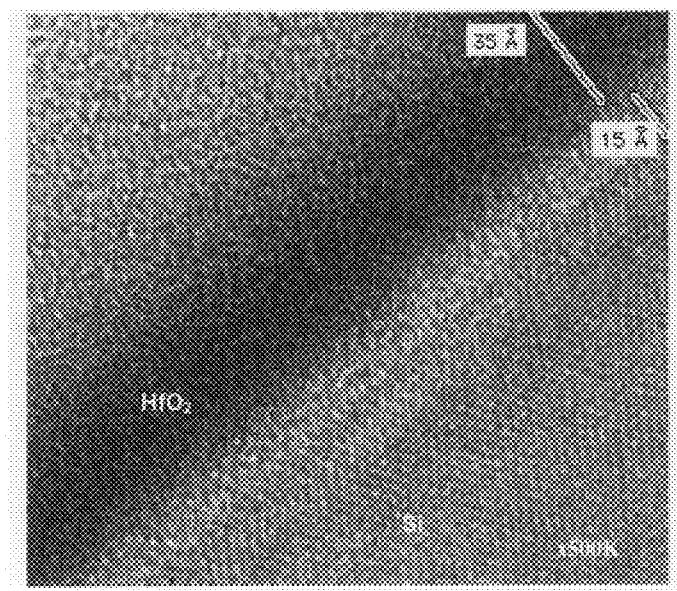
FIG. 11 illustrates TEM results for a wafer annealed at 700° C.

For the comparison between RCSE and TEM two wafers were prepared. Both consisted of nominally 35 Å thick HfO$_2$ films on c-Si substrates, with the first annealed at 500° C. and the second at 700° C. Quarters of each wafer were measured by TEM and RCSE. The TEM result for the wafer annealed at 700° C. is shown in FIG. 11. From the micrograph we find thicknesses of 35 and 15 Å for the HfO$_2$ and interface thicknesses, respectively. These agree well with the thicknesses 40 and 12 Å, respectively, determined by RCSE.

Figure 12:
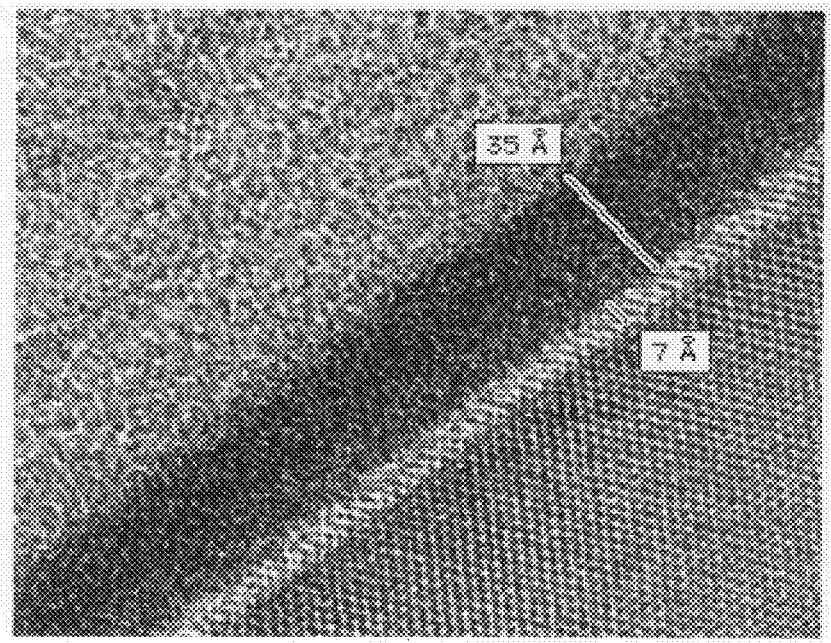
FIG. 12 illustrates TEM results for a wafer annealed at 500° C.

The TEM result for the wafer annealed at 500° C. is shown in FIG. 12. Here, the HfO$_2$ and interfaces are again 35 and 7 Å, respectively. The corresponding thicknesses determined by RCSE are 33 and 9 Å, again in reasonable agreement with the TEM results.

Conclusions for Example 2

We have demonstrated that, with proper dispersions for the HfO$_2$ film and its interface with c-Si, we can measure the thicknesses of both simultaneously with RCSE. The results are in good agreement with TEM results on the same wafers. This indicates that RCSE can be used as an in-line monitoring tool for ultrathin gate oxides of the high-k material HfO$_2$.

We claim:

1. A method of evaluating parameters of a semiconductor sample including a silicon substrate and an oxide layer formed thereon comprising the steps of:

optically inspecting the sample and generating a set of actual measured data;

generating a set of theoretical data based upon a set of theoretical parameters and a theoretical model which includes representations for the silicon substrate, the oxide layer and an interface layer therebetween, where the representation of the interface layer includes the electronic structure of the silicon as modified by the interface layer characteristics;

comparing the set of measured data to the set of generated theoretical data and determining the differences therebetween; and repeating the generating and comparing steps, wherein the theoretical parameters chosen for the subsequent generating step are selected so that the theoretical data becomes increasingly more similar to the measured data.

2. A method as recited in claim 1, wherein the step of optically inspecting the sample includes obtaining spectroscopic ellipsometric measurements.

3. A method as recited in claim 1, wherein the step of optically inspecting the sample includes obtaining spectroscopic measurements.

4. A method as recited in claim 1, wherein the step of generating theoretical data is performed using Fresnel equations.

5. A method as recited in claim 1, wherein the step of comparing the data is performed using a least squares fitting algorithm.

6. A method as recited in claim 1, wherein the oxide layer is formed from a material selected from the group consisting of silicon oxide, halfnium oxide, zirconium oxide, tantalum oxide, titanium oxide, strontium-titanium oxide, and barium-strontium-titanium oxide.

7. A method as recited in claim 1, wherein said oxide layer is less than 30 angstroms thick.

8. A method as recited in claim 1, wherein said oxide layer is a gate oxide.

9. A method as recited in claim 1, wherein the representation of the electronic structure of the silicon includes a multiple peak structure wherein the silicon peaks are shifted and broadened.

10. A method as recited in claim 1, wherein the representation of the interface layer includes a five peak critical point model.

11. A method of evaluating parameters of a semiconductor sample including a silicon substrate and an oxide layer formed thereon comprising the steps of:

optically inspecting the sample and generating a set of actual measured data;

generating a set of theoretical data based upon a set of theoretical parameters and a theoretical model which includes representations for the silicon substrate, the oxide layer and an interface layer therebetween, where the representation of the interface layer includes the critical point multiple peak structure of the silicon as modified by the interface layer characteristics;

comparing the set of measured data to the set of generated theoretical data and determining the differences therebetween; and repeating the generating and comparing steps, wherein the theoretical parameters chosen for the subsequent generating step are selected so that the theoretical data becomes increasingly more similar to the measured data.

12. A method as recited in claim 11, wherein the step of optically inspecting the sample includes obtaining spectroscopic ellipsometric measurements.

13. A method as recited in claim 11, wherein the step of optically inspecting the sample includes obtaining spectroscopic measurements.

14. A method as recited in claim 11, wherein the step of generating theoretical data is performed using Fresnel equations.

15. A method as recited in claim 11, wherein the step of comparing the data is performed using a least squares fitting algorithm.

16. A method as recited in claim 11, wherein the oxide layer is formed from a material selected from the group consisting of silicon oxide, halfnium oxide, zirconium oxide, tantalum oxide, titanium oxide, strontium-titanium oxide, and barium-strontium-titanium oxide.

17. A method as recited in claim 11, wherein said oxide layer is less than 30 angstroms thick.

18. A method as recited in claim 11, wherein said oxide layer is a gate oxide.

19. A method as recited in claim 11, wherein the peaks of the silicon structure are shifted and broadened for the interface layer.

20. A method as recited in claim 11, wherein the representation of the interface layer includes a five peak critical point model.

21. A method of evaluating parameters of a semiconductor sample including a silicon substrate and an oxide layer formed thereon comprising the steps of:

optically inspecting the sample and generating a set of actual measured data;

generating a set of theoretical data based upon a set of theoretical parameters and a theoretical model which includes representations for the silicon substrate, the oxide layer and an interface layer therebetween, where the representation of the interface layer includes dispersion curves having a multiple peak critical point structure of the silicon as modified by the characteristics of the interface layer;

comparing the set of measured data to the set of generated theoretical data and determining the differences therebetween; and repeating the generating and comparing steps, wherein the theoretical parameters chosen for the subsequent generating step are selected so that the theoretical data becomes increasingly more similar to the measured data.

22. A method as recited in claim 21, wherein the step of optically inspecting the sample includes obtaining spectroscopic ellipsometric measurements.

23. A method as recited in claim 21, wherein the step of optically inspecting the sample includes obtaining spectroscopic measurements.

24. A method as recited in claim 21, wherein the step of generating theoretical data is performed using Fresnel equations.

25. A method as recited in claim 21, wherein the step of comparing the data is performed using a least squares fitting algorithm.

26. A method as recited in claim 21, wherein the oxide layer is formed from a material selected from the group consisting of silicon oxide, halfnium oxide, zirconium oxide, tantalum oxide, titanium oxide, strontium-titanium oxide, and barium-strontium-titanium oxide.

27. A method as recited in claim 21, wherein said oxide layer is less than 30 angstroms thick.

28. A method as recited in claim 21, wherein said oxide layer is a gate oxide.

29. A method as recited in claim 21, wherein the peaks of the silicon structure in the dispersion curves are shifted and broadened for the interface layer.

30. A method as recited in claim 21, wherein the representation of the interface layer includes a five peak critical point model.

* * * * *